United States Patent
Brydon

(10) Patent No.: US 6,237,593 B1
(45) Date of Patent: *May 29, 2001

(54) ESTIMATION OF FLOW AND DETECTION OF BREATHING CPAP TREATMENT

(75) Inventor: John William Ernest Brydon, Waverton (AU)

(73) Assignee: ResMed Limited, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/052,891

(22) Filed: Mar. 31, 1998

Related U.S. Application Data

(63) Continuation-in-part of application No. 08/348,580, filed on Dec. 2, 1994, now Pat. No. 5,740,795.

(30) Foreign Application Priority Data

Dec. 3, 1993 (AU) .................................................. PM2793

(51) Int. Cl.$^7$ .................................................. A61M 16/00
(52) U.S. Cl. .............................. 128/204.22; 128/204.18; 128/204.21; 128/204.24
(58) Field of Search .................. 128/204.22, 204.21, 128/204.23, 204.24, 204.18, 205.24, 205.25; 600/529, 532, 536; 607/20

(56) References Cited

U.S. PATENT DOCUMENTS

| | | | |
|---|---|---|---|
| 3,741,208 | * 6/1973 | Jonsson et al. | ................ 128/204.21 |
| 3,817,246 | 6/1974 | Weigl . | |
| 3,882,847 | 5/1975 | Jacobs . | |
| 3,903,875 | 9/1975 | Hughes . | |
| 3,914,994 | 10/1975 | Banner . | |
| 3,932,054 | 1/1976 | McKelvey . | |
| 3,985,467 | 10/1976 | Lefferson . | |
| 4,387,722 | 6/1983 | Kearns . | |
| 4,414,982 | 11/1983 | Durkan . | |
| 4,448,058 | 5/1984 | Jaffe et al. . | |

(List continued on next page.)

FOREIGN PATENT DOCUMENTS

| | | |
|---|---|---|
| 52628/93 | 7/1994 | (AU) . |
| 39130/95 | 6/1996 | (AU) . |
| 3015279 A1 | 10/1981 | (DE) . |
| 3537507 A1 | 4/1987 | (DE) . |
| WO 94/16759 | 8/1994 | (DE) . |

(List continued on next page.)

OTHER PUBLICATIONS

Derwent: Flowmeter for fluids–has turbine transducer and volumetric sensor for simultaneous calibration.

Mark Kantrowitz, Erik Horskotte and Cliff Joslyn, "Answers to Frequently Asked Questions About Fuzzy Logic and Fuzz Expert System", Version 1.24, last modified Feb. 20, 1996.

Primary Examiner—Dennis Ruhl
Assistant Examiner—V. Srivastava
(74) Attorney, Agent, or Firm—Pillsbury Winthrop LLP

(57) ABSTRACT

Apparatus and methods for the estimation of flow and the detection of breathing (respiration) in continuous positive airway pressure (CPAP) treatment are disclosed. CPAP apparatus typically includes a flow generator for supplying air to a mask via a gas delivery tube. With changing air flow, the flow generator's speed and/or driving electrical current will alter in a manner defined by the controlling circuitry. Signals can be derived from measurements of motor speed and current, and these signals vary cyclically with patient respiration. By filtering to reject non-respiratory components, the resultant signal can be utilized to determine the instants in time at which the patient starts to inhale and exhale. The filtered signal also can be linearized using a predetermined knowledge of the pressure/flow/speed characteristics of the flow generator, and thus to derive a volumetric measure of airflow.

14 Claims, 6 Drawing Sheets

U.S. PATENT DOCUMENTS

| | | |
|---|---|---|
| 4,499,914 | 2/1985 | Schebler . |
| 4,558,710 | 12/1985 | Eichler . |
| 4,630,614 | 12/1986 | Atlas . |
| 4,648,407 | 3/1987 | Sackner . |
| 4,677,975 | 7/1987 | Edgar et al. . |
| 4,686,999 | 8/1987 | Snyder et al. . |
| 4,795,314 | 1/1989 | Prybella et al. . |
| 4,803,471 | 2/1989 | Rowland . |
| 4,819,629 | 4/1989 | Jonson . |
| 4,823,788 | 4/1989 | Smith et al. . |
| 4,825,802 | 5/1989 | Le Bec . |
| 4,827,922 | 5/1989 | Champain et al. . |
| 4,860,766 | 8/1989 | Sackner . |
| 4,870,960 | 10/1989 | Hradek . |
| 4,915,103 | 4/1990 | Visveshwara et al. . |
| 4,938,210 | 7/1990 | Shene . |
| 4,938,212 | 7/1990 | Gnook et al. . |
| 4,957,107 | 9/1990 | Sipin . |
| 4,972,842 | 11/1990 | Korten et al. . |
| 4,986,269 | 1/1991 | Hakkinen . |
| 5,063,922 | 11/1991 | Hakkinen . |
| 5,105,354 | 4/1992 | Nishimura . |
| 5,134,995 | 8/1992 | Gruenke et al. . |
| 5,174,287 | 12/1992 | Kallok et al. . |
| 5,178,138 | 1/1993 | Walstrom et al. . |
| 5,231,983 | 8/1993 | Matson et al. . |
| 5,245,995 * | 9/1993 | Sullivan et al. ............... 128/205.25 |
| 5,265,594 * | 11/1993 | Olsson et al. .................. 128/204.18 |
| 5,280,784 | 1/1994 | Kohler . |
| 5,293,864 | 3/1994 | McFadden . |
| 5,322,057 | 6/1994 | Raabe et al. . |
| 5,388,571 | 2/1995 | Roberts et al. . |
| 5,404,871 | 4/1995 | Goodman et al. . |
| 5,438,980 | 8/1995 | Phillips . |
| 5,443,075 | 8/1995 | Holscher . |
| 5,479,920 | 1/1996 | Piper et al. . |
| 5,509,404 | 4/1996 | Lloyd et al. . |
| 5,540,220 | 7/1996 | Gropper . |
| 5,549,106 | 8/1996 | Gruenke et al. . |
| 5,570,682 | 11/1996 | Johnson . |
| 5,608,647 | 3/1997 | Rubsamen et al. . |
| 5,630,411 | 5/1997 | Holscher . |
| 5,642,730 | 7/1997 | Baran . |
| 5,655,520 | 8/1997 | Howe et al. . |
| 5,660,171 | 8/1997 | Kimm et al. . |
| 5,666,946 | 9/1997 | Langenback . |
| 5,701,883 | 12/1997 | Hete et al. . |
| 5,704,345 | 1/1998 | Berthon-Jones . |
| 5,730,121 | 3/1998 | Hawkins . |
| 5,740,795 * | 4/1998 | Brydon ........................... 128/204.21 |
| 5,797,852 | 8/1998 | Karakasoglu et al. . |
| 5,803,066 | 9/1998 | Rapoport et al. . |
| 5,845,636 | 12/1998 | Gruenke et al. . |

FOREIGN PATENT DOCUMENTS

| | | |
|---|---|---|
| 0 066 451 A1 | 12/1982 | (EP) . |
| 0 164 500 A2 | 3/1985 | (EP) . |
| 0 236 850 A2 | 9/1987 | (EP) . |
| 298 367 A2 | 1/1989 | (EP) . |
| 481 459 A1 | 4/1992 | (EP) . |
| 606 687 A2 | 7/1994 | (EP) . |
| 178 925 A2 | 4/1996 | (EP) . |
| 0 839 545 A1 | 5/1998 | (EP) . |
| 2 672 221 | 8/1992 | (FR) . |
| 2682042 A1 | 4/1993 | (FR) . |
| 1432572 | 4/1976 | (GB) . |
| 2 077 444 | 12/1981 | (GB) . |
| 2 164 569 | 3/1986 | (GB) . |
| 2 254 700 | 10/1992 | (GB) . |
| 2 261 290 | 5/1993 | (GB) . |
| 54-104369 | 8/1979 | (JP) . |
| 62-103297 | 4/1987 | (JP) . |
| 63-275352 | 11/1988 | (JP) . |
| 4-70516 | 3/1992 | (JP) . |
| 467041 | 5/1992 | (SE) . |
| WO 82/03326 | 10/1982 | (WO) . |
| WO 86/06969 | 12/1986 | (WO) . |
| WO 92/15353 | 9/1992 | (WO) . |
| WO 96/16688 | 6/1996 | (WO) . |

* cited by examiner

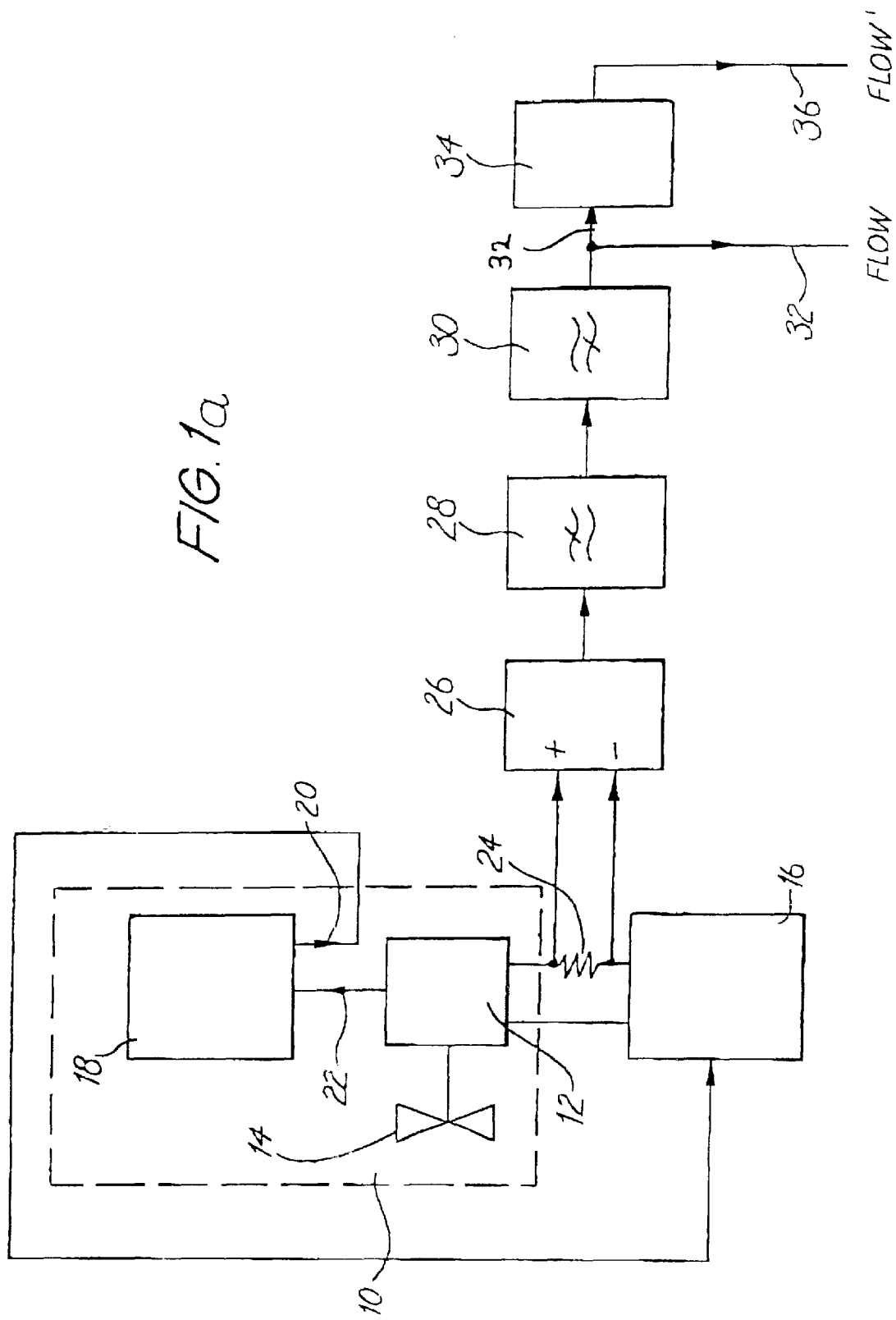

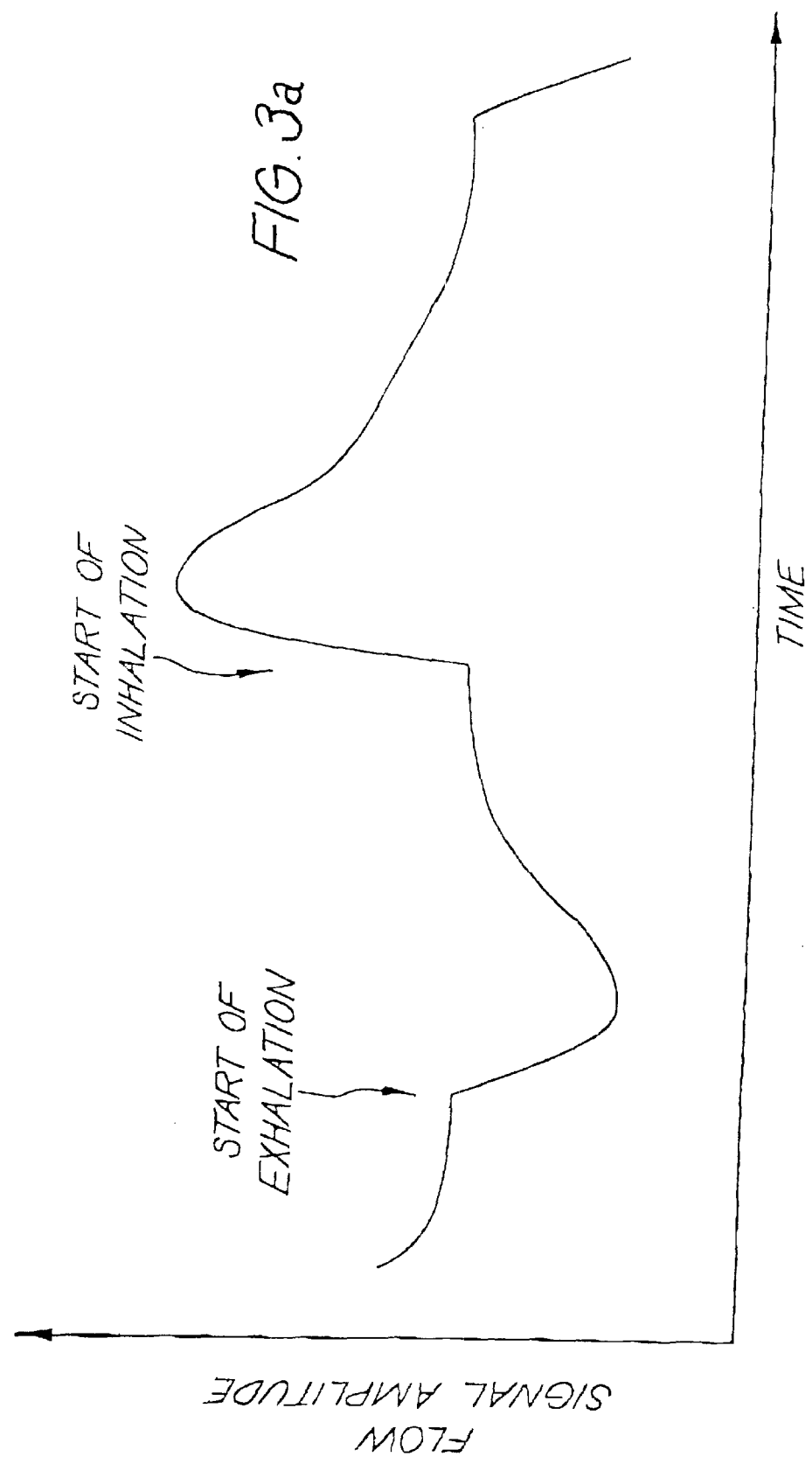

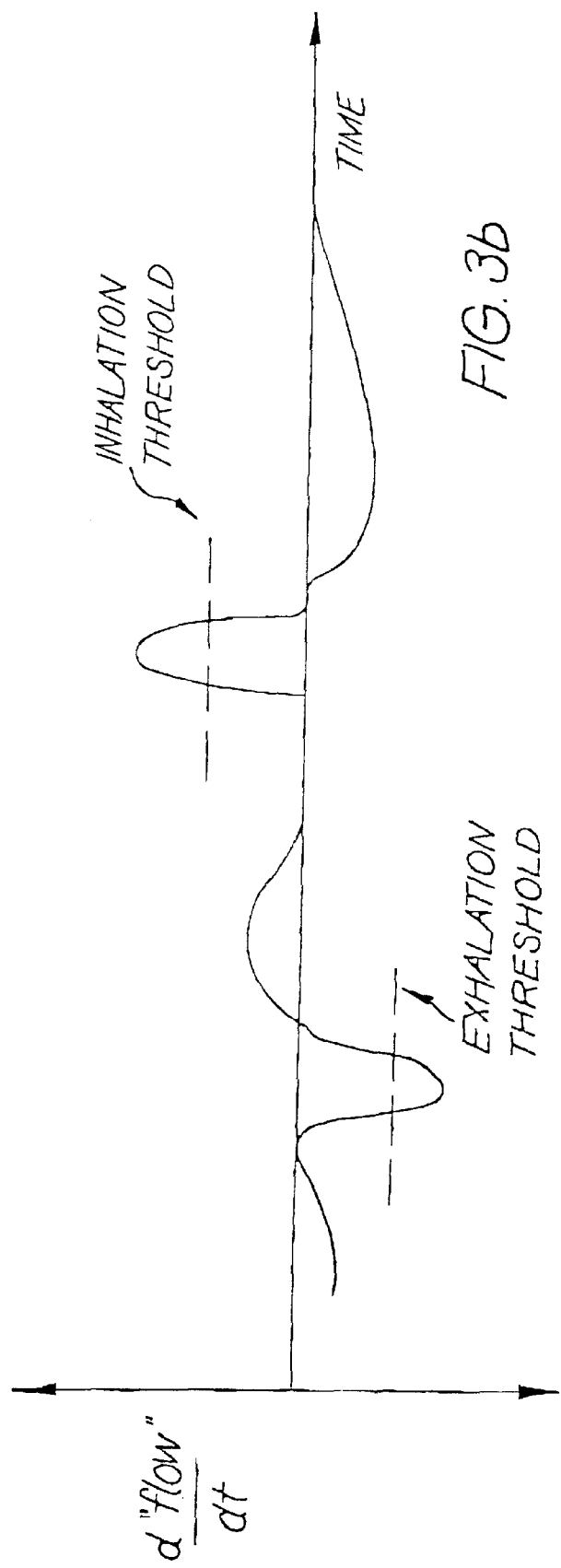

ESTIMATION OF FLOW AND DETECTION OF BREATHING CPAP TREATMENT

RELATED APPLICATION

This application is a continuation-in-part of U.S. Ser. No. 08/348,580, filed Dec. 2, 1994 issued as U.S. Pat. No. 5,740,795.

FIELD OF THE INVENTION

This invention relates to methods and apparatus for the determination of volumetric respiratory flow during assisted respiration, including continuous positive airway pressure (CPAP) treatment.

BACKGROUND OF THE INVENTION

The administration of CPAP is common in the treatment of Obstructive Sleep Apnea (OSA) syndrome and Upper Airway Resistance syndrome. CPAP treatment may be considered as one form of assisted ventilation generally. The fundamental disclosure of CPAP is made in the specification of PCT/AU82/00063, published under WO 82/03548. CPAP treatment effectively acts as a pneumatic splint of a patient's upper airway by the provision of a positive air pressure a approximately 10 cm $H_2O$, although pressures in the range of approximately 2–20 cm $H_2O$ are encountered. More sophisticated forms of CPAP, such as bi-level CPAP and autosectting CPAP, are described in U.S. Pat. No. 5,245,995. Common to all forms of CPAP is a nose, mouth or face mask fitted to a patient having connection via a flexible air delivery tube to an air flow generator.

In more advanced forms of CPAP treatment, the measurement of airflow in the air delivery tube is used to detect the average volume breathed by the patient and to determine whether that person is inhaling (inspiring) or exhaling (expiring). Currently this is done using an in-line sensor to measure flow directly, or by measuring the pressure drop across a restriction in the air delivery tube (or alternatively, the pressure drop along the air delivery tube). These methods require the use of additional transducers and, in some cases, additional wiring or tubing to connect the transducer to the appropriate point in the circuit. A determination of respiratory flow determined in this way can lead to the determination of patient volumetric flow, which is a clinically useful metric.

In this specification any reference to a "mask" is to be understood as embracing a nose, mouth or combination nose and mouth (face) mask suitable for the administration of CPAP treatment. Furthermore, a "mask" can include nasal prongs (cannulae) that are inserted into the nares at the entrance to the airway.

Finally, CPAP treatment may occur at a single pressure or multiple pressures, such as in bilevel or autosetting treatments.

SUMMARY OF THE INVENTION

It is a preferred object of the present invention to offer an improvement over existing methods at least by removing the need for additional transducers, wires or tubing to measure airflow and, in turn, volumetric respiratory airflow.

Therefore the invention discloses a method for determination volumetric respiratory flow during the administration of continuous positive airway pressure (CPAP) treatment by CPAP apparatus, said method comprising the steps of:

providing a flow generator for supplying breathable gas to a mask via a gas delivery tube;

measuring an electrical parameter indicative of power consumed by said flow generator to derive a power signal;

filtering said power signal to remove non-respiratory components; and linearising said filtered signal with respect to a predetermined characteristic of said gas delivery tube and said mask relating flow to consumed power to provide a volumetric measure of respiratory flow.

The invention further discloses an apparatus for the detection of respiration during the administration of CPAP treatment by a CPAP system, said apparatus comprising:

a flow generator for supplying breathable gas to a mask via a gas delivery tube;

means for measuring an electrical parameter indicative of power consumed by said flow generator and deriving a power signal thereof;

means for filtering said power signal to remove non-respiratory components; and means for linearising said filtered signal with respect to a signal of a predetermined characteristic of said gas delivery tube relating flow to consumed power to provide a measure of respiratory flow.

BRIEF DESCRIPTION OF THE DRAWINGS

Embodiments of the invention will now be described with reference to the accompanying drawings, in which:

FIGS. 1*a* and 1*b* are schematic diagrams of two flow detection systems;

FIGS. 3*a* and 3*b* are graphs of airflow, and the time derivative of airflow.

DETAILED DESCRIPTION OF PREFERRED EMBODIMENTS AND BEST MODE

A CPAP flow generator typically is realised by a small turbine powered by an electric motor. The speed of the motor is controlled by a feedback loop in that either the motor speed or the air pressure in the breathing circuit is measured and an error signal generated to increase or decrease drive to the motor or other regulating device, thus attempting to maintain either a constant motor speed or a constant CPAP treatment delivery pressure. Airflow in the breathing circuit is normally dictated by one or more of:

a) a constant, deliberate leak situated near the mask (or at the end of the nasal prongs) to ensure that patient rebreathing is minimal;

b) the patient's respiration; and c) any additional unintended leaks.

With changing airflow due to respiration, parameters such as the turbine motor's speed and/or current will alter in a manner defined by the motor or solenoid-operated spill valve control circuitry. The solenoid-operated spill valve has the function of maintaining constant delivery pressure.

Signals can be derived from the motor speed and power measurements, or from the spill valve position and power measurements. These measured signals vary cyclically with the patient's respiration. In general they also bear a non-linear relationship to the actual volumetric flow which can, if required, be linearized (as hereinafter described) using previously determined pressure/flow/speed characteristics of the turbine system to give a volumetric measure of patient respiration (flow).

Without linearization, the signal can be used to detect the points at which the patient starts to inhale and exhale. These points are crucial to the correct working of bi-level CPAP machines which present to the patient a smaller pressure at exhalation than inhalation, and in machines which seek to automatically vary the CPAP pressure in line with the patient's clinical needs. The cyclical variation of the respiratory component in the signal is extracted by identifying the more slowly changing non-respiratory component and subtracting this from the original signal. Alternatively, the minimum value of the cyclic component can be detected and stored and thereafter subtracted from the original signal.

Figure 1B:
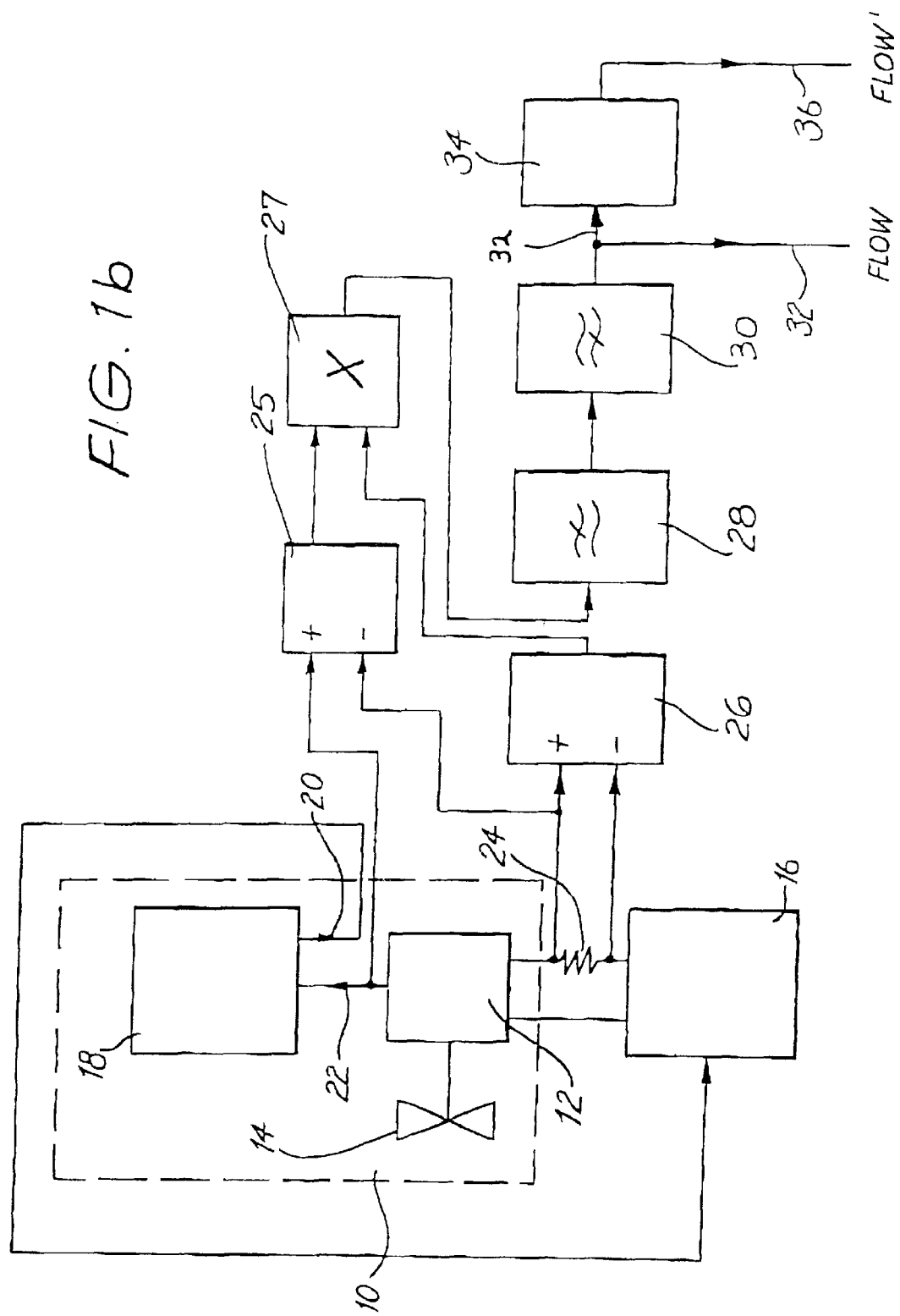

Embodiments implementing this methodology are shown in the accompanying drawings. In FIGS. 1a and 1b, a flow generator 10 comprises an electric motor 12 that drives a turbine 14. The turbine 14 provides a supply of pressurised air (or breathable gas) for the administration of CPAP treatment, transported to the patient's mask by an air delivery tube (not shown). The motor 12 receives electrical power from a power supply 16. Also comprising a part of the flow generator 10 is a motor controller 18, which issues a control signal 20 to the power supply 16 to control the motor speed and thus the speed of the turbine 14 and, in turn, the flow rate in the air delivery tube. Furthermore, a speed feedback signal 22 is input to the motor controller 18 to provide a signal upon which speed regulation can be based.

As shown in FIG. 1a, one of the interconnecting wires between the power supply 16 and the motor 12 is provided with a current sensing resistor 24. This resistor therefore detects current demanded by the motor 12, represented as the voltage appearing across the resistor 24. That voltage is sensed and input to a differential amplifier 26, thus producing an output signal representative of motor current (and thus also motor power). This output signal is then provided to a low-pass filter circuit 28 having an upper limiting frequency of, say, 20 Hz. The low-pass filter circuit 28 removes high frequency electrical noise, and also tends to average the signal. The filtered signal is then passed through a high-pass filter 30, typically with 0:5 Hz cut-off, to remove the non-respiratory components. The output signal 32 from the high-pass filter 30 is labelled FLOW.

FIG. 1b shows an alternative arrangement to that shown in FIG. 1a. Optionally, the voltage drop across the motor 12 also can be measured via a differential amplifier 55. The output voltage thereof is then multiplied with the motor current signal previously derived by the differential amplifier 26 by a multiplier 27 to produce a measure of the time instantaneous power consumed by the motor. This time instantaneous power signal then is provided to the low pass filter circuit 28, and processing proceeds as described above. In many implementations, current alone will be a sufficient indicator of motor power, however in other cases the real instantaneous power will advantageously be determined as shown in FIG. 1b.

The FLOW output signal 32, is supplied to an inhalation/exhalation detector (not shown) which functions to determine the start of inhalation and exhalation by locating the sudden changes of signal amplitude and/or polarity following a segment having a low rate of change with time and being of a given minimum duration, typically 0.2 second. FIG. 3a shows a typical flow characteristic, and identifies both the start of inhalation and exhalation events, that are detected by the methodology described. Therefore, the FLOW output signal 32 provides an indication of the instances of inhalation and exhalation, and these points are critical to the correct working of bi-level CPAP machines, for example.

Alternatively, the output from the low-pass filter 28 can be input to a negative peak detector (not shown) which triggers a sample and hold circuit (also not shown) to latch the minimum point of the respiratory fluctuation. The detected minimum point of respiratory fluctuation can be updated periodically, typically as an exponentially past-time weighted sum of present and previous minimum measurements.

Figure 2:
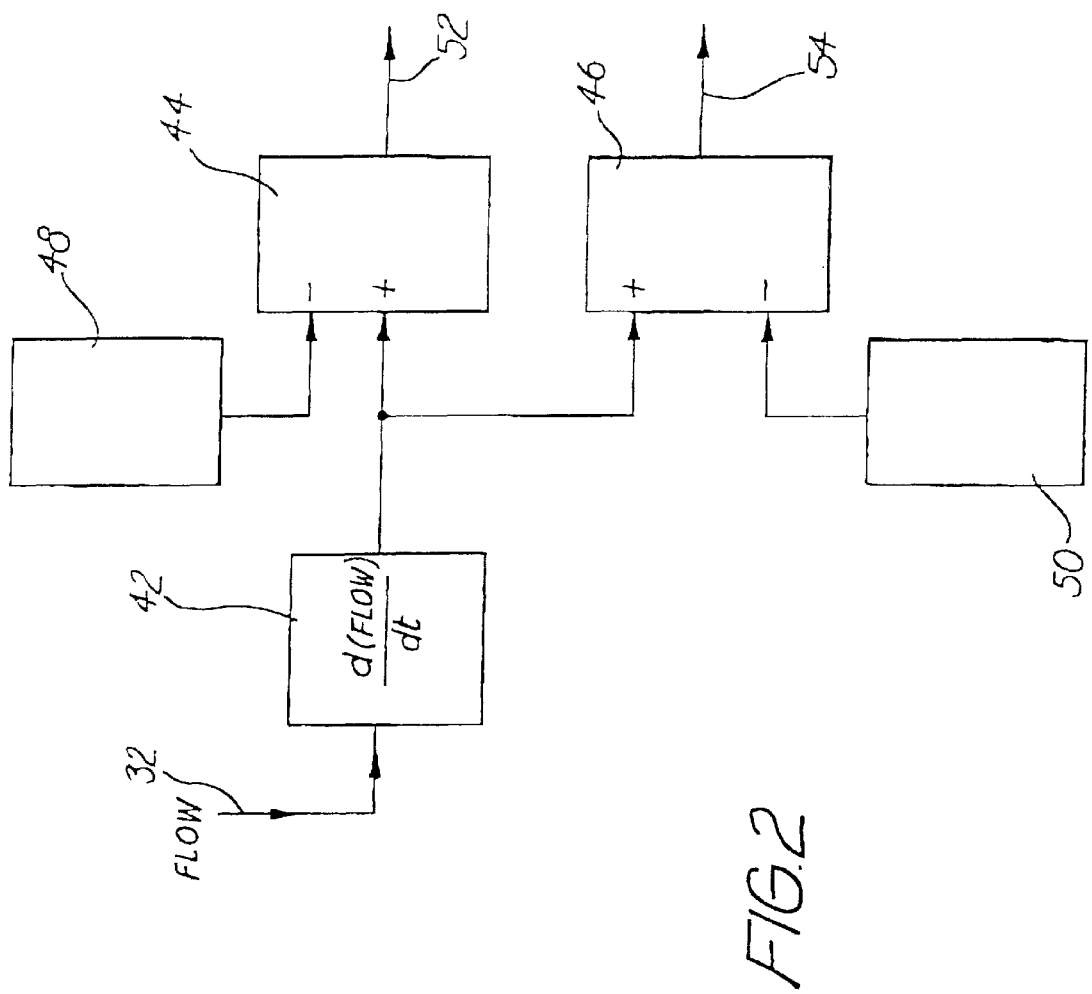
FIG. 2 is a schematic diagram of an inhalation/exhalation detector.

FIG. 2 shows another method and apparatus for the detection of inhalation and exhalation events. As shown, a band-limited differentiator 42 receives the FLOW' signal 36, derived from the high-pass filter circuit 30. The output from the differentiator 42 is supplied to a pair of comparators 44,46. This output signal, as a time differential, is represented in FIG. 3b. Associated with each comparator 44,46 is a threshold generator 48,50. These generators 48,50 respectively have a threshold value for detecting inhalation and exhalation, as is shown in FIG. 3b. Therefore, the comparator 44 will compare the time differentiated flow signal output from the differentiator 42 with the threshold value supplied by the threshold generator 48, and when that value is exceeded (in the negative sense) an inhalation detection signal 52 is output. The other comparator 46 functions in a similar way to output an exhalation detection signal 54 in the event that the time differentiator flow signal exceeds (in a positive sense) the threshold value set by the threshold generator 50.

In another embodiment, the low-pass filtered signal (the output of the low-pass filter 28) derived from the motor current can be digitised and input to a microcomputer where the subsequent signal processing described above is performed digitally. In this implementation threshold levels and decision times can be varied dynamically to track the changing shape of the patient's respiratory flow.

As shown in FIGS. 1a and b, the output signal 32 also is provided to a linearization element 34 to produce a linearized flow signal 36 (FLOW') which gives a volumetric measure of patient respiration by comparison with a previously determined pressure/flow/speed characteristics of the turbine system as will be presently discussed.

In relation to the linearization element 34, the following discussion is instructive.

A physical variable such as flow or pressure is often measured as the output signal (often electrical) produced by a suitable transducer.

If the amplitude of the said output signal varies in constant proportion to the said physical variable then the measurement system is said to be linear. In this case, therefore, if the physical variable increases by a factor, k, then the output signal also increases by that same factor. The mathematical relationship between the physical variable and the output signal is expressed by the linear equation:

[Physical-Variable]=[constant]×[Output Signal]

In another class of transducers the output signal of the transducer does not bear a mathematically linear relationship to the amplitude of the physical variable being measured. Some flow transducers, for example, produce an output signal that varies as the square of the physical variable, that is, the flow. In this case the mathematical relationship between the physical variable and the output signal is expressed by the linear equation:

[Physical Variable]=[constant]×SquareRoot(Output Signal)

In complex transducer systems the mathematical relationship between the output signal and the physical variable (or variables) may be complicated mathematical function determined either from theory or by experiment. This relationship is generalised to:

[Physical Variable]=function(Output Signal)

Figure 4:
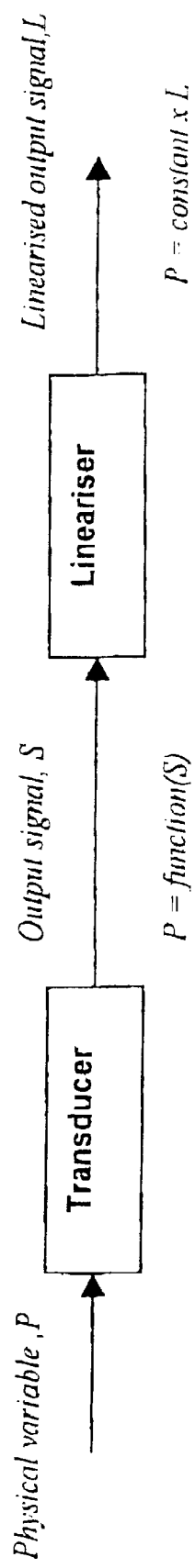
FIG. 4 shows a mathematical sequence for the linearization process.

In most practical transducer systems an output signal is preferred which varies in constant proportion to the physical variable being measured, that is it has a mathematically linear relationship thereto. If the output signal does not possess this simple linear relationship then it can be subjected to an additional process, the output of which does bear the required linear relationship to the physical variable being measured. The said additional process is called a linearizer in recognition of its function. The said linearizer may take the form of an analog circuit or a software program within a computer or microprocessor. FIG. 4 shows a graphical representation of such a linearization process.

The linearization element 34 performs a single dimension linearization, the function of which is derived from the pressure/flow/speed characteristic of the turbine system comprising the turbine 14, air delivery tube and mask. This three dimensional characteristic is determined empirically.

I claim:

1. A method for determination volumetric respiratory flow during the administration of continuous positive airway pressure (CPAP) treatment by CPAP apparatus, said method comprising:

providing a flow generator for supplying breathable gas to a mask via a gas delivery tube;

measuring an electrical parameter indicative of power consumed by said flow generator to derive a power signal;

filtering said power signal to remove non-respiratory components; and linearising said filtered signal with respect to a predetermined characteristic of said gas delivery tube and said mask relating flow to consumed power to provide a volumetric measure of respiratory flow.

2. The method of claim 1, whereby said predetermined characteristic is obtained from a pressure/flow/speed characteristic of a turbine system providing said CPAP treatment.

3. The method of claim 2, further comprising:

detecting a change in said filtered signal to give a signal indicative of respiration;

comparing said change signal with a first threshold value to detect start of inhalation phase if said first threshold value is exceeded; and comparing said change signal with a second threshold value to detect start of exhalation phase if said second threshold value is exceeded.

4. The method of claim 3, whereby said detecting step is performed by differentiation.

5. The method of claim 4, wherein said first threshold value is positive and said second threshold value is negative so that when said differentiated signal is compared with said positive threshold value and is greater than said first threshold value that is determinative of start of inhalation phase, and when said differentiated signal is compared with said negative threshold value and is less than said negative threshold value that is determinative of the start of the exhalation phase.

6. The method of claim 5, whereby said filtering step comprises high-pass filtering said power signal.

7. An apparatus for the detection of respiration during the administratior of CPAP treatment by a CPAP system, said apparatus comprising:

a flow generator for supplying breathable gas to a mask via a gas delivery tube;

means for measuring an electrical parameter indicative of power consumed by said flow generator and deriving a power signal thereof;

means for filtering said power signal to remove non-respiratory components; and means for linearising said filtered signal with respect to a signal of a predetermined characteristic of said gas delivery tube relating flow to consumed power to provide a measure of respiratory flow.

8. The apparatus of claim 7, wherein said predetermined characteristic is obtained from a pressure/flow/speed characteristic of said flow generator, gas delivery tube and mask.

9. The apparatus of claim 8, further comprising:

means for detecting a change in said filtered signal to give a signal indicative of respiration;

means for comparing said change signal with a first threshold value to detect start of inhalation phase if said first threshold value is exceeded; and means for comparing said change signal with a second threshold value to detect start of exhalation phase if said second threshold value is exceeded.

10. The apparatus of claim 9, wherein said means for detecting a change in said filtered signal is a differentiator.

11. The apparatus of claim 10, further wherein said first threshold value is positive and said second threshold value is negative so that when said differentiated signal is compared with said positive threshold value and is greater than said first threshold value that is determinative of start of inhalation phase, and when said differentiated signal is compared with said negative threshold value and is less than said second threshold value that is determinative of start of exhalation phase.

12. The apparatus of claim 11, wherein said filter means is a high-pass filter.

13. The method of claim 1 wherein said supplying step includes supplying breathable gas at at least two different pressures.

14. The apparatus of claim 7 wherein said apparatus further includes:

means to deliver pressure to the mask at at least two different pressure values.

* * * * *